US010195302B2

(12) United States Patent
Murrell

(10) Patent No.: US 10,195,302 B2
(45) Date of Patent: Feb. 5, 2019

(54) METHOD AND APPARATUS FOR DISINFECTION

(71) Applicant: Specialist Hygiene Solutions Limited, Kings' Lynn, Norfolk (GB)

(72) Inventor: Tim Murrell, Dersingham (GB)

(73) Assignee: SPECIALIST HYGIENE SOLUTIONS LIMITED (GB)

(*) Notice: Subject to any disclaimer, the term of this patent is extended or adjusted under 35 U.S.C. 154(b) by 0 days.

(21) Appl. No.: 14/381,334

(22) PCT Filed: Feb. 27, 2013

(86) PCT No.: PCT/GB2013/050477
§ 371 (c)(1),
(2) Date: Aug. 27, 2014

(87) PCT Pub. No.: WO2013/128179
PCT Pub. Date: Sep. 6, 2013

(65) Prior Publication Data

US 2015/0017060 A1 Jan. 15, 2015

(30) Foreign Application Priority Data

Feb. 27, 2012 (AU) ................................ 2012100211
Feb. 29, 2012 (GB) .................................. 1203542.4

(51) Int. Cl.
*A61L 9/14* (2006.01)
*A61L 9/12* (2006.01)

(52) U.S. Cl.
CPC ................ *A61L 9/14* (2013.01); *A61L 9/122* (2013.01); *A61L 2209/211* (2013.01)

(58) Field of Classification Search
CPC ........................................................ A61L 9/14
USPC ............................................................. 422/3
See application file for complete search history.

(56) References Cited

U.S. PATENT DOCUMENTS 5,492,273 A * 2/1996 Shah .................... F24F 11/0009 236/11
2004/0050951 A1* 3/2004 Almero .................. B05B 12/00 239/69
2008/0038166 A1* 2/2008 Hill ......................... A61L 2/208 422/292
2011/0114744 A1 5/2011 Ricciardi et al.

FOREIGN PATENT DOCUMENTS

WO 2004062800 A1 7/2007
WO 2009138430 A1 11/2009
WO 2011047127 A1 4/2011

* cited by examiner

*Primary Examiner* — Sean E Conley
*Assistant Examiner* — Holly M Mull
(74) *Attorney, Agent, or Firm* — Tarolli, Sundheim, Covell && Tummino LLP

(57) ABSTRACT

A process and apparatus for disinfection of spaces using a disinfecting liquid droplet spray atomization are described, in which an electric fan 107 is used to dispense the atomization from an atomization chamber 104 via venture outlets 106 into the space to be disinfected. The operation of the electric fan 107 is modulated in a substantially random sequence to vary the rate of dispensing into the space in order to improve the dispersal of the atomized droplets in the space and hence the efficacy of disinfection.

7 Claims, 5 Drawing Sheets

METHOD AND APPARATUS FOR DISINFECTION

BACKGROUND

The present invention relates to a method and apparatus for disinfecting spaces such hospital rooms and the like.

The problem of micro-organism contamination of, for example, hospital bedrooms and the like has gown into an acute one in recent years and one particular method of disinfecting such spaces and any equipment located therein is the use of disinfecting sprays (atomisations) of liquid droplets such as hydrogen peroxide. These systems are often known as hydrogen peroxide fogging systems and such hydrogen peroxide fogging systems can involve vaporization of a low concentration hydrogen peroxide solution using a high frequency ultrasound (typically 1.6-2 MHz) droplet generator in an atomization chamber partially filled with solution. WO-A-2009-138430 discloses such a system and method designed to provide improved efficacy of such methods and which involves the steps of: (a) determining a first value of the relative humidity of the air in the space; (b) atomizing a disinfecting liquid in the space until a predetermined second value of the relative humidity of the air is reached in the space, and; (c) maintaining the relative humidity of the air for a predetermined time at the second value by means of atomizing the disinfecting liquid, wherein the method further comprises of decreasing the relative humidity of the air in the space prior to and/or during atomizing of the disinfecting liquid.

In such processes, under the influence of the ultrasonic droplet generator and through the mechanism of forced cavitation, small sized droplets (circa 1 μm diameter) are produced and ejected from the solution surface. Airflow from an electric fan then carries these droplets as a mist from the chamber via a venturi into the space to be treated. A combination of the fan's airflow and natural convection currents in the room carry these droplets until they contact surfaces where they are deposited and operate to destroy any organisms present. Given appropriate generating capacity for the space to be disinfected, if sufficient vaporised hydrogen peroxide is expelled from the system, statistically a good fog density and hence hydrogen peroxide distribution will be achieved in the space.

This traditional process is controlled via a closed loop system, with relative humidity (RH) being the controlling variable as described in WO-A-2009-138430. Tests have shown that in a closed environment (which is required for safety), RH increase is proportional to hydrogen peroxide concentration increase.

One of the primary factors affecting efficacy of the process is the profile of the airflow within the space being treated. Traditionally, with a regular electric fan operating in a closed space with no external ventilation (as required for safety), a reasonably static air distribution pattern is achieved which, depending on the layout of the room and its contents, can lead to areas of poor fogging coverage and hence droplet deposition, a phenomenon known as spatial differentiation and this in turn can lead to incomplete disinfection.

SUMMARY OF THE INVENTION

According to the present invention, a process for disinfection of spaces using a disinfecting liquid droplet spray (atomisation), in which a fan is used to dispense the atomisation into the space to be disinfected, can be improved by modulating the operation of the electric fan in a substantially random sequence.

Apparatus for carrying out the method comprises a hydrogen peroxide fogging device having an electric fan for dispensing a fog of hydrogen peroxide droplets into a space to be disinfected, and a control system for modulating the operation of the electric fan in a substantially random sequence.

Preferably, apparatus for carrying out the process includes a venturi injector into which atomized droplets are introduced as a secondary airflow and the electric fan is arranged to provide a primary flow of entraining air through the venturi into which the atomized droplets are entrained for dispensing into the space to be disinfected.

This is preferably achieved by controlling the 'duty cycle', i.e. the ON/OFF cycle of operation of the fan in accordance with a pseudo-random sequence. This may have the effect of adjusting the fan speed, depending on the time periods being used. Alternatively, the fan speed may be varied directly by adjusting the electrical power supplied to it in accordance with a desired pseudo random characteristic.

During the fog generation phase of treatment, the microcontroller controls the fan speed to create the required the turbulent airflow.

The random sequence may, as in the current embodiment, be provided by a software pseudo random number generator running on the control system hardware. This is used to switch the electric fan on and off using a pulse-width modulation scheme determined by the pseudo random number generator, the pulse width being determined, on each successive cycle of on/off times, by the random number generator. Using a pulse width modulation scheme with a relatively short (say 1-3 second) period for both 'ON' and 'OFF' parts of the cycle, causes the fan's speed-up and speed-down ramps to overlap, which gives rise to variable air speed.

This higher fog density in conjunction with optimisation by the control system of the attained humidity level to match the ambient temperature of the space, gives rise to microcondensation on surfaces in the space being treated. This has been shown to increase efficacy of the decontamination process.

While pulse width modulation is preferred, other methods of achieving the randomized airflow profile may be used.

Randomization of the airflow has the effect of improving dissipation by introducing a more dynamic airflow, which greatly reduces the number of poor coverage areas by creating a more turbulent and random airflow within the space. Also, the atomization droplet density being expelled from the machine is being constantly changed (whilst maintaining the sub 1 μm droplet size required for mobility). This further assists with creating a dynamic, turbulent airflow.

Preferably, additionally, the attained RH is based upon the air temperature of the space being treated, and the desired RH target is linked to the ambient temperature of the space being treated.

Once the mist generation phase is complete, it is required to allow a period of time for deactivation of the hydrogen peroxide where it breaks back down into water and oxygen. During this time, the fan is controlled to operate at normal, i.e. full, single speed, operation, to maximise airflow and to minimise deactivation time.

The combination of fan modulation and venturi, gives the advantage that with a constant atomisation/fog generation rate, during the low fan speed/pwm off periods a higher fog density builds in the venturi, and is expelled as the fan speed re-increases. Given the random nature of the fan speed, the fog density is constantly changing, which also assists with generation of a turbulent airflow profile.

BRIEF DESCRIPTION OF THE ACCOMPANYING FIGURES

Figure 1:
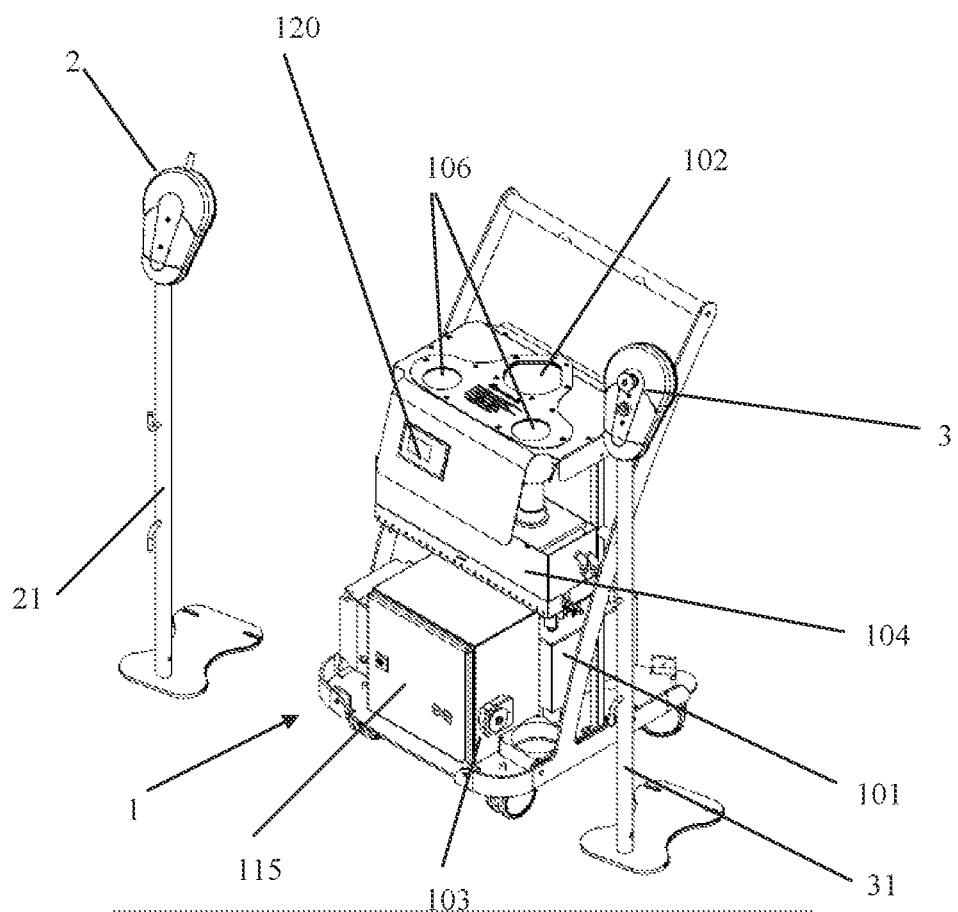
FIG. 1 is a perspective view of apparatus according to the invention, from the front.
Figure 2:
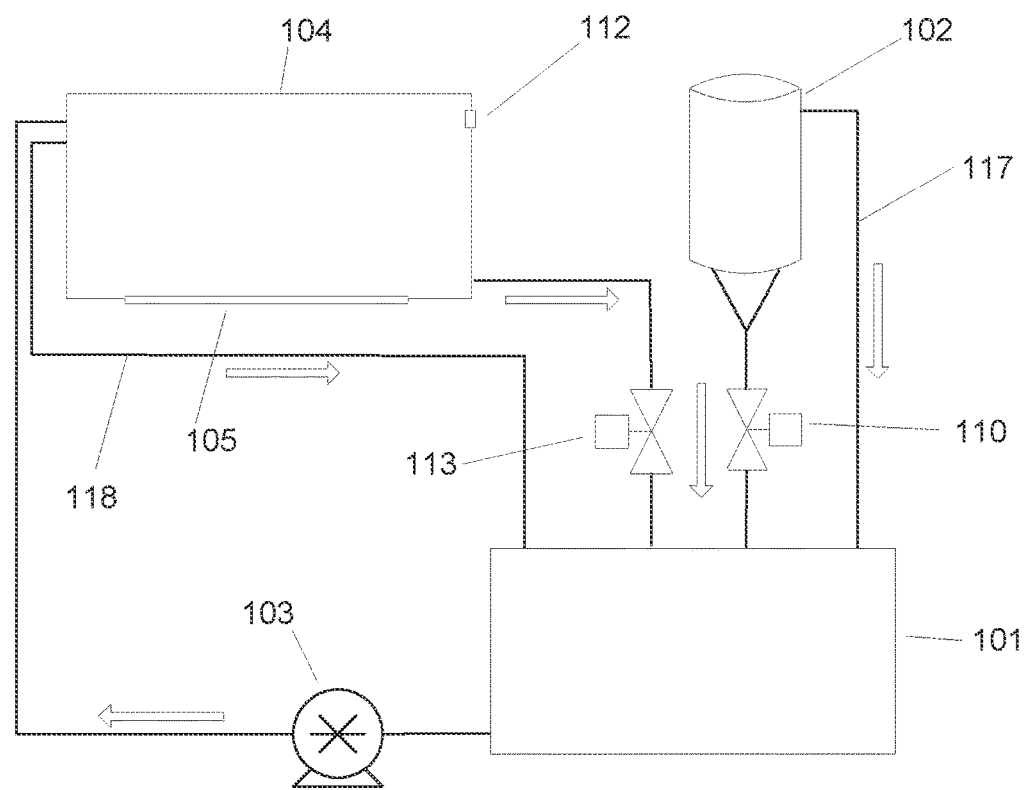
FIG. 2 is a block diagram illustrating flow of hydrogen peroxide within the apparatus and the corresponding components.
Figure 3:
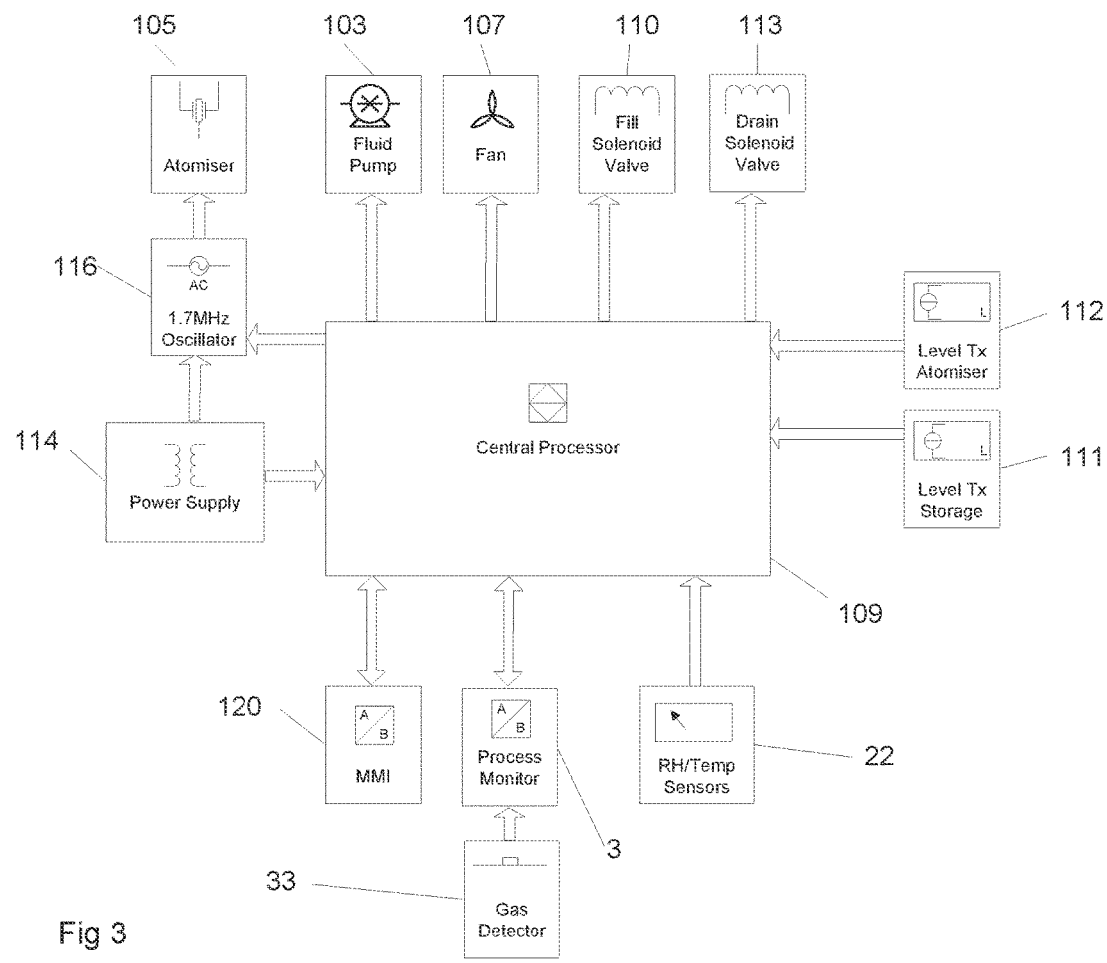
FIG. 3 is a block diagram illustrating the main components of the atomisation, delivery and control components of the apparatus.
Figure 4:
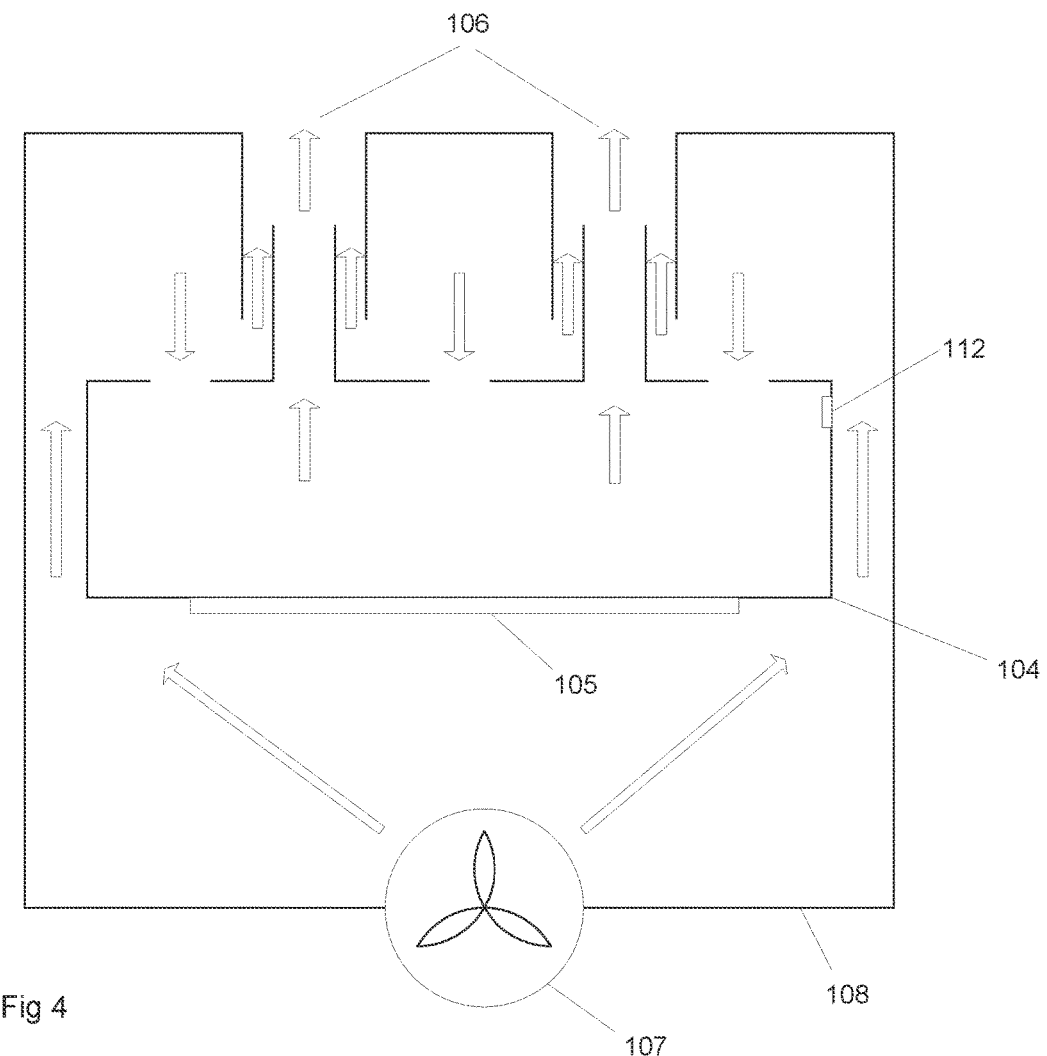
FIG. 4 is diagrammatic view illustrating the arrangement of the atomization unit of the apparatus.
Figure 5:
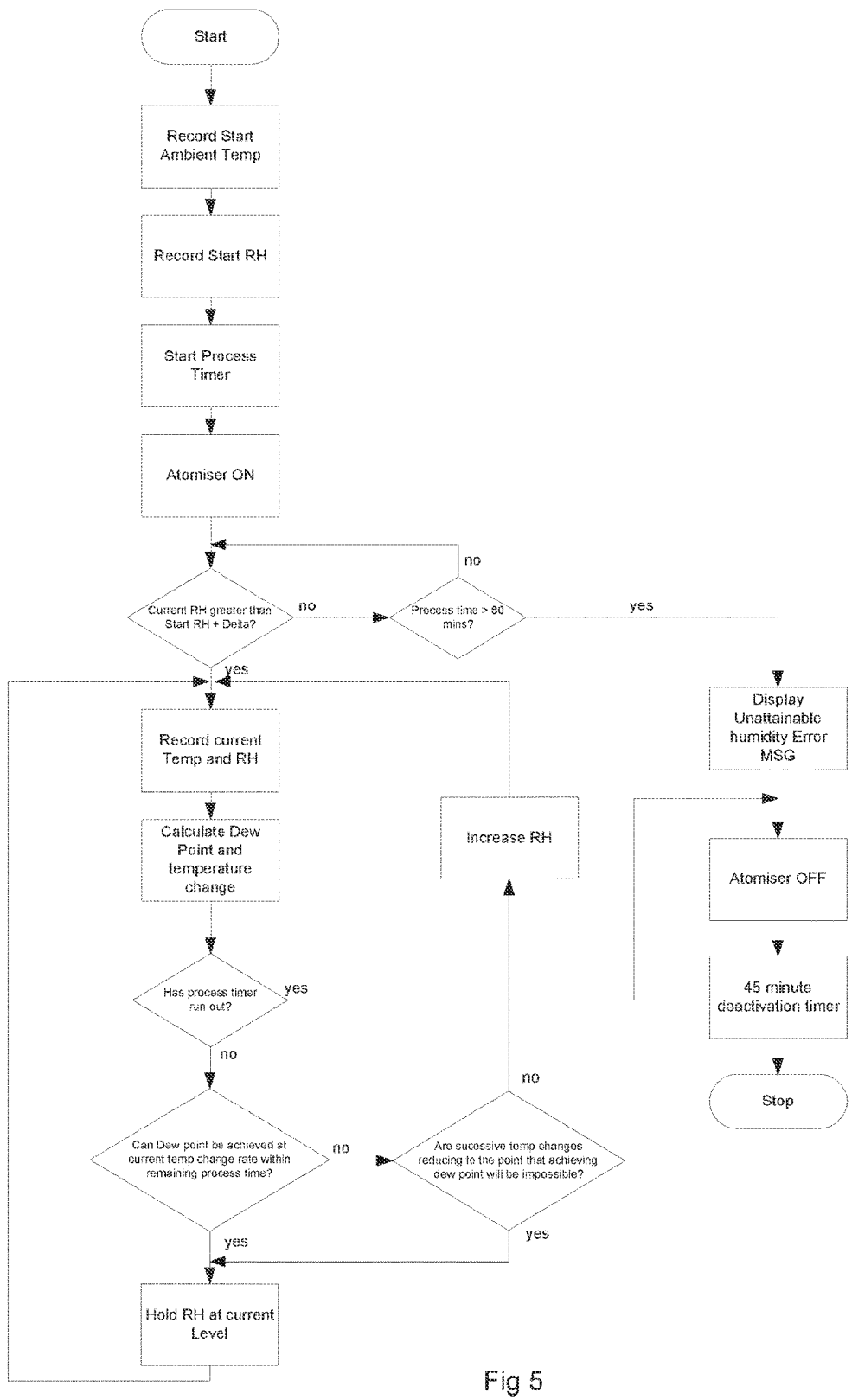
FIG. 5 is a flowchart of the disinfecting process.

DETAILED DESCRIPTION

One example of apparatus according to the invention will now be described with reference to the accompanying figures described above.

The apparatus has a portable fogging unit 1 mounted on a trolley 10, a portable relative humidity and temperature sensor unit 2 on a stand 21, and a remote control and indication unit (or process monitor) 3, likewise on a stand 31. In use, the portable fogging unit 1 and the humidity sensor unit 2 are disposed within a space to be disinfected and the remote control and indication unit 3 is disposed outside the space which is sealed from the surrounding area for safety. The control and indication unit 3 includes a hydrogen peroxide monitor 33 arranged, on detecting hydrogen peroxide gas outside of the space under treatment, to provide a signal to the fogging unit 1 to halt operation of the apparatus.

The fogging unit 1 includes a storage reservoir 101 for liquid hydrogen peroxide and which is supplied from a hydrogen peroxide cartridge 102. A pump 103 is provided to supply hydrogen peroxide from the storage reservoir to an atomization chamber 104, in the base of which is provided an ultrasonic atomization unit 105. This operates in use, to generate high frequency ultrasound (typically at 1.6-2 MHz) to cause cavitation in the liquid hydrogen peroxide in the atomization chamber and hence creates a fog of atomized droplets above the level of the liquid in the atomization chamber. To create a hydrogen peroxide 'fog' within the space to be disinfected, a pair of venturi injection outlets 106 are provided, the primary (or entraining) airflow through which is provided by a fan 107 disposed within a housing 108 surrounding the atomization chamber 104. Atomized droplets entrained in the primary airflow are emitted into the atmosphere in the space to be disinfected and, in use, alight on surfaces within the space, causing those surfaces to be disinfected. The atomized droplets preferably have a diameter of around 1 μm. Overflow lines 117,118 from the cartridge 102 and atomization chamber 104 respectively back into the storage reservoir 101 are provided to prevent overflow/spillage in case of control system failure.

The fogging unit carries a power supply 114 housed in a casing 115 and supplying power for driving the various electrical components including an oscillator 116 which in turn drives the atomization unit 105. The fogging unit 1 also includes a user interface in the form of a control panel and display 120 which provides instructions and information on the status of the operation to the operator during the setup and post-decontamination phases. It also displays error and warning messages. As it is not accessible during the process (being inside the space under decontamination), information is provided via a data cable (not shown) to the process monitor 3 which thus gives status information to the operator from outside the space during the disinfection process.

Having now described the main components, the operation of the apparatus will now be described.

Before the treatment begins, the space to be treated is prepared by sealing doors, ventilation openings etc. and by placing the portable fogging unit 1 and the relative humidity and temperature sensor unit 2 in the space, the relative humidity and temperature sensor unit being located remote from the fogging unit 1. The process monitor 3 (remote control and indication unit) is placed outside the space to be treated.

At the start of the process a control switch (not shown) on the fogging unit 1 is operated and, via a signal to a microcontroller 109 which in turn activates a control valve 110, hydrogen peroxide liquid is admitted to the storage reservoir 101 from the supply cartridge 102. The control valve 110 allows the liquid hydrogen peroxide to enter the reservoir 101, with an electronic level sensor 111 transmitting a signal reporting reservoir level to the microcontroller 109. Multiple supply cartridges may be used before the desired level is reached in the storage reservoir 101 and the control valve 110 is closed once sufficient cartridges have been drained into the system to fill the storage reservoir.

Once the reservoir 101 is filled to the desired level as determined by the sensor 111, the control system microcontroller 109 commands the pump 103 to fill the atomization chamber 104 to a predetermined level (in this example 53-57 mm). The level in the atomization chamber 104 is communicated to the control system microcontroller 109 via a level sensor 112. Once the correct level is attained, the pump 103 is stopped and the system enters the standby state. Personnel are removed from the space and it is finally sealed.

The decontamination cycle is then started by a key operated switch on the process monitor 3. Indicators on the process monitor show the current status of the system during use. The decontamination cycle starts by reading the initial relative humidity value of the space from sensor in the RH and temperature sensor unit 2 which includes a transmitter 22 connected to the microcontroller 109, and by operating the atomization unit 105 in the atomization chamber 104. At the same time the duty cycle of the fan 107 is pseudo-randomly varied by pulse width modulating the electrical supply to the fan.

Fog generated in the atomization chamber 104 is expelled into the space under treatment by the action of the fan 107 and venturi outlets 106.

The optimum relative humidity is determined based on current temperature measured from RH sensor unit and other programmable parameters as described below in relation to the flowchart of FIG. 5. When this RH level is attained, the atomization unit 105 in the atomization chamber 104 is controlled in a closed loop system including the microcontroller 109 to hold this level accurately for the duration of the active phase of the process (90 minutes in the current example). The atomization unit preferably includes multiple transducers disposed over the bottom of the atomization chamber, but all driven by the same input signal. The fluid level in the atomization chamber 104 is also held at 53-57 mm by a closed loop control system between the pump 103, level sensor 112 and the central processor 109.

The process works by logging the starting humidity and running the atomization unit 105 until a predetermined RH difference above the ambient is reached (typically this is the relative humidity at start plus 25%). The humidity is then maintained at this level for a predetermined time period set into the control system (typically 60-90 minutes). The control system microcontroller also logs the ambient temperature. Once the desired RH level is reached and rather than just holding this RH level static, changes in ambient temperature can be monitored to change the setpoint of the atomization RH control system. The process is illustrated in the flowchart of FIG. 5 which is self-explanatory.

Since heating and ventilation to the space under treatment is blocked/disabled during a disinfection process, the temperature generally falls over the course of a disinfection cycle. This can be improved by heating the space prior to decontamination, and removing the source of heat just prior to starting decontamination. In practice, the dew point may be approximated by: $T_{dew}=T_{ambient}-(100-RH/5)$, which, although not dimensionally correct, has been found, as a rule of thumb approximation to be generally accurate to within a degree or so, as long as the RH is over 50% (which it is at the point in the process where the approximation is used). This is sufficiently accurate to fulfil the requirements of the control system. It is desirable to achieve micro-condensation on surfaces where possible to improve efficacy (this occurs significantly at the dew point), the control system microcontroller 109 monitors the rate of change of ambient temperature via the RH and temperature sensor unit 2, and attempts to attain an RH value which gives rise to the dew point being achieved during the process as the temperature falls. For example, if the RH (after the initial period of increase) is 70%, the change in temperature over a 5 minute period has been −0.5° C., the current ambient temperature is 20° C., and there is 45 minutes of process time remaining, the dew point will be approximately 14 degrees. With a temp loss of 0.1° C./minute one would need 60 minutes to reach the dew point, but only 45 minutes remain. The control system calculates the required RH to achieve the dew point within the remaining time at the current rate of change of temperature. In this case, the temperature would drop by only 4.5 degrees (assuming a fixed rate of change), so the RH would need to be increased to 77.5% to achieve dew point during the process. Of course, rate of change of temperature during the process is not constant and will reduce as thermal equilibrium is approached. The control system is adaptive and constantly changing based upon the above relationship. It may not be possible to achieve dew point for every disinfection operation (if there is little or no ambient temperature change during the process), and in this case, the control system will timeout on attempting to achieve dew point and hold a ceiling RH.

When the active phase is completed, the atomization unit 105 is turned off, and the fan modulation ceases, with the fan 107 then being driven to provide a full 120 m³/hr for a further deactivation period (45 minutes in the current example), while the hydrogen peroxide breaks down. Whilst this deactivation period is current, the control system microcontroller 109 instructs control valve 113 to open, draining any remaining fluid from the atomization chamber 104 back into the storage reservoir 101 for subsequent re-use.

After this deactivation period, signals on the process monitor 3 indicate to the operator that it is safe to return to the space. During the set up and post process phases, the control panel and display 120 provides instructions to the operator, and also displays and warning/error messages.

In the current example, tests have shown a random fan operating time between 1 and 3 seconds to be optimal, with pauses of similar length (also randomly determined by the pulse width modulator). This range allowing a 750 ml volume (chamber capacity above liquid level) to be fog filled between fan cycles, gives an increased fog density as compared to running the atomizer with a fan running permanently at the full 120 m³/hr rate.

The invention claimed is:

1. A process for disinfection of spaces using a disinfecting liquid droplet spray atomization, in which an electric fan is used to dispense the atomization into the space to be disinfected, wherein the speed of the fan is controlled in accordance with a pseudo-random number generator for adjusting the speed of the fan, and wherein the fan is operated by a pulse-width-modulated (PWM) signal having an ON part with an associated ON period and an OFF part with an associated OFF period, and wherein the ON period and the OFF period are each specified by the pseudo-random number generator and are each of a duration in the range of about one second to about three seconds.

2. A process according to claim 1, in which the duty cycle of the fan is modulated in accordance with the pseudo-random number generator.

3. A process according to claim 1, wherein the fan is operated by a pulse- width-modulated (PWM) signal the period of which is in accordance with the pseudo-random number generator.

4. A process according to claim 1, in which atomized droplets are introduced into a venturi injector and the fan creates a primary flow of entraining air through the venturi and into which the atomized droplets are entrained for dispensing into the space to be disinfected.

5. A process according to claim 1, in which the relative humidity of the air within the space is determined prior to the fan starting.

6. A process according to claim 1, in which status information is provided to a display outside of the space under treatment.

7. A process according to claim 1, in which a hydrogen peroxide monitor is disposed outside of the space under treatment and is arranged so that, on detecting hydrogen peroxide gas outside of the space under treatment, the process is halted.

* * * * *